United States Patent [19]

Baldwin et al.

[11] 4,234,590

[45] Nov. 18, 1980

[54] THIOSUBSTITUTED PYRIDINES

[75] Inventors: John J. Baldwin; Gerald S. Ponticello, both of Lansdale, Pa.

[73] Assignee: Merck & Co., Inc., Rahway, N.J.

[21] Appl. No.: 9,008

[22] Filed: Feb. 5, 1979

[51] Int. Cl.³ .................... C07D 213/89; A61K 31/44
[52] U.S. Cl. .................................. 424/263; 546/296; 546/303
[58] Field of Search .................. 546/296; 424/263

[56] References Cited

U.S. PATENT DOCUMENTS

| | | | |
|---|---|---|---|
| 4,000,282 | 12/1976 | Baldwin | 260/294.8 |
| 4,060,601 | 11/1977 | Baldwin | 260/294.8 |
| 4,115,575 | 9/1978 | Frei et al. | 260/294.8 |

FOREIGN PATENT DOCUMENTS 1305644 2/1973 United Kingdom .
1492352 11/1977 United Kingdom .

*Primary Examiner*—John M. Ford
*Attorney, Agent, or Firm*—Daniel T. Szura; Harry E. Westlake, Jr.

[57] ABSTRACT

3-Trifluoromethylthio-2-(3-loweralkylamino-2-$R_1$O-propoxy)pyridines, their pharmaceutically acceptable salts certain intermediates and their preparation are disclosed. These pyridines have pharmaceutical properties such as antihypertensive activity of rapid onset.

8 Claims, No Drawings

THIOSUBSTITUTED PYRIDINES

BACKGROUND OF THE INVENTION

The present invention concerns 3-CF$_3$S-2-(3-loweralkylamino-2-R$_1$O-propoxy)pyridines having pharmaceutically useful properties, certain intermediates and their preparation.

Hypertension in man and other animals can be treated with various chemical agents. One such class of agents is that known as the β-adrenergic blocking agents or β-blockers. While this class of agents can have antihypertensive activity, the onset of this activity is generally gradual. The structure and activity of β-blockers is generally discussed in "Clinical Pharmacology and Therapeutics" 10, 252, 306 (1969). Substituted N-heteroaryl β-adrenergic blocking agents are disclosed in U.S. Pat. No. 4,000,282, U.S. 4,060,601, German application No. 2,406,930, its counterpart South African patent No. 74 28204, British Pat. No. 1,305,644, Journal of Medicinal Chemistry 16, 1113-1114 (1973) and Journal of Medicinal Chemistry 15, 1321 (1972).

Novel 3-CF$_3$S-2-(3-loweralkylamino-2-R$_1$O-propoxy)pyridines have been discovered. These compounds have antihypertensive activity of rapid onset and are β-adrenergic blocking agents.

SUMMARY OF THE INVENTION

3-CF$_3$S-2-(3-loweralkylamino-2-R$_1$O-propoxy)-pyridines their pharmaceutical use, certain intermediates and their preparation.

DESCRIPTION OF THE PREFERRED EMBODIMENTS

An embodiment of the present invention is compounds having the formula

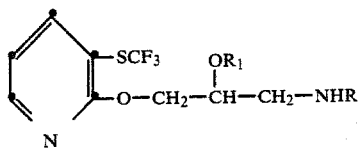

I wherein
R is C$_1$-C$_6$ alkyl, preferably C$_3$-C$_4$ branched alkyl and
R$_1$ is H or

wherein L is C$_1$C$_{10}$ alkyl, phenyl and substituted phenyl having up to two substituents which are independently selected from C$_1$-C$_4$ alkoxy, halo and C$_1$C$_4$ alkyl
and pharmacuetically acceptable salts thereof.

The L group includes C$_1$-C$_{10}$, linear and branched, hydrocarbon alkyl such as methyl, n-decyl, tert. butyl, isoamyl, n-heptyl and the like with C$_1$-C$_4$ alkyl being preferred, and mono- and di-substituted phenyl such as 4-tert. butylphenyl, 2,6-dibromophenyl, 3-methylphenyl, 4-n-propylphenyl, 3,5-dimethoxyphenyl, 4-iodophenyl, 2-methyl-4-chlorophenyl, 4-fluorophenyl and the like, with mono-substituted phenyl preferred. Compounds where R$_1$ is H are most preferred.

R is isopropyl, sec. butyl,CH$_3$,tert. butyl, C$_6$H$_{11}$, with tert. butyl being most preferred.

Examples of useful Formula I compounds are

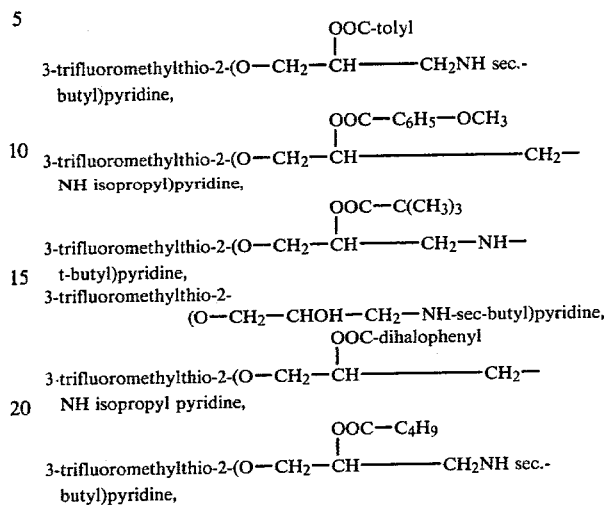

and the like.

Preferred compounds of formula I are those where R is isopropyl or tert butyl. More preferred compounds are those where R$_1$ is H.

The especially preferred compounds are those wherein R is isopropyl or t-butyl and R$_1$ is H; and the most preferred compound has the formula

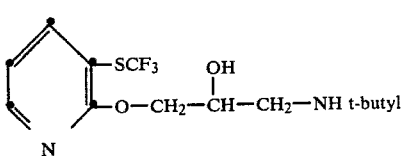

II

The Formula I pyridines of the present invention include all the optical isomer forms, that is mixtures of enantiomers e.g. racemates as well as the individual enantiomers. These individual enantiomers are commonly designated according to the optical rotation they effect, by (+) and (−), (L) and (D), (l) and (d) or combinations of these symbols. The symbols (S) and (R) stand for sinister and rectus respectively and designate an absolute spatial configuration of the enantiomer. The (S) isomer form is the more preferred form.

The pyridines of the present invention can be prepared by any convenient process.

One such process involves the coupling of a halopyridine with a suitable substituted oxazolidine and hydrolysing the reaction product obtained. The process yields Formula I compounds where R$_1$ is H and is illustrated by the following set of reaction equations:

Reaction Sequence A (1)

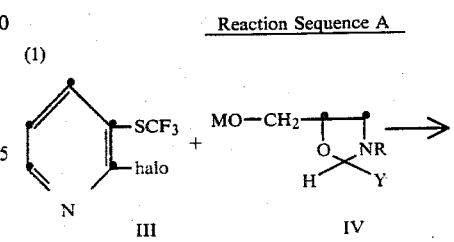

-continued
Reaction Sequence A

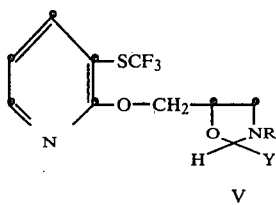

(2)

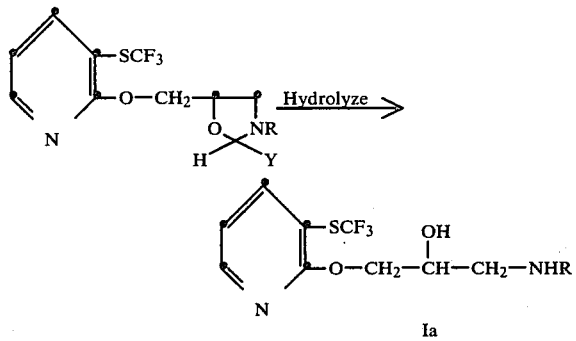

Halo may be Cl or Br, with Br being preferred. M is an alkali metal, either potassium or sodium. Y can be hydrogen or the residue of any suitable aldehyde

e.g. an arylaldehyde, such as benzaldehyde, naphthaldehyde and the like, or an alkanal such as acetaldehyde, butyraldehyde and the like. The process for preparing oxazolidines where M is hydrogen is disclosed in U.S. Pat. No. 3,718,647, U.S. Pat. No. 4,000,282, U.S. Pat. No. 3,657,237 and U.S. Pat. No. 4,060,601 and to the extent necessary the pertinent disclosure is incorporated herein by reference. The alkali metal salt of the oxazolidine is prepared in a conventional manner by reaction of the corresponding hydroxymethyloxazolidine with an appropriate amount of an alkali base reactant. However, this Reaction A may also be carried out with in-situ formation of the alkali metal oxazolidine salt (Formula IV) by reacting the oxazolidine

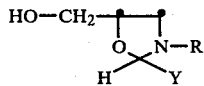

VI with the Formula III pyridine in the presence of a strong base which as an alkali metal alkoxide (e.g. K—O—C—(CH$_3$)$_3$) or sodium hydride.

The coupling reaction can be carried out at temperatures ranging from about 0° to about 100° C. A temperature range of about 10° to about 50° C. is preferred. The reaction is generally carried out in a solvent. Any suitable solvent may be used. Examples of useful solvents are dimethylformamide, dimethylsulfoxide, hexamethylphosphoramide, tert. butanol, alkanols and the like. The hydrolysis is carried out using conventional acid hydrolysis reagent and techniques e.g. treatment with a solution of any strong mineral acid such as HCl or H$_2$SO$_4$. The hydrolysis product can be directly obtained as the salt of the acid used for the hydrolysis. Ordinarily, the product Ia is recovered as the free base after conventional neutralization of the salt.

The coupling reaction is ordinarily carried out at atmospheric pressure. Higher pressures may be used is desired.

When a racemic oxazolidine (Formula IV or VI) is used as a reactant, the product is obtained as a racemate. The racemate may be separated into its individual enantiomers by conventional resolution techniques.

By using a single optical isomer of said oxazolidine in the above reactions, the product may be obtained directly as a single enantiomer. Thus, if the S-isomer of the oxazolidine is used, then the product obtained will be the S-isomer. This provides a convenient way for directly preparing individual isomers of the present pyridines.

Pyridines of the present invention wherein R$_1$ is other than hydrogen are conveniently prepared by treating the corresponding pyridine where R$_1$ is hydrogen with an appropriate acylating agent such as an acyl halide, e.g. undecanoyl chloride, pivaloyl chloride, benzoylchloride, p-methoxybenzoyl chloride, an anhydride e.g. acetic anhydride, and the like. The reaction is illustrated by the following equations:

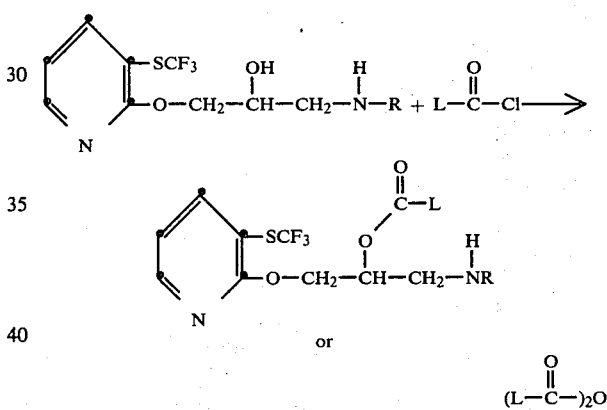

The compounds of the present invention also include the pharmaceutically acceptable salts of the novel pyridines. These salts are generally salts of the Formula I pyridines and organic or inorganic acids. These salts are prepared by treating the pyridine with an appropriate amount of a useful acid, generally in a suitable solvent. Examples of useful organic acids are carboxylic acids such as maleic acid, acetic acid, tartaric acid, propionic acid, fumaric acid, isethionic acid, succinic acid, pamoic acid, oxalic acid, pivalic acid and the like; useful inorganic acids are hydrohalo acids such as HCl, HBr, HI; sulfuric acid, phosphoric acid and the like. The hydrochloride and hydrogen maleate salts are examples of preferred salts.

The compounds of the present invention have antihypertensive activity of rapid onset and are also β-adrenergic blocking agents. One advantage the present pyridines have over ordinary β-adrenergic blocking agents is that the antihypertensive effect is immediate and generally of extended duration.

This rapid onset antihypertensive activity is determined by administering (orally) a representative pyridine of the present invention to spontaneously hypertensive (SH) rats and measuring the effect on blood pressure. An example of a representative compound having this antihypertensive activity is (S)-2-(3-tert.butylamino-2-hydroxypropoxy)-3-trifluoromethylthiopyridine.

The β-adrenergic blocking activity of the Formula I pyridines is determined by measuring the ability of a representative pyridine to block isoproterenol induced β-adrenergic stimulant effects such as heart rate increase, hypotension and bronchodilation, in animals.

The ability of the Formula I pyridines to reduce blood pressure, in an SH rat, rapidly and for extended duration, indicates that the present pyridines and their salts are useful to treat hypertension in humans. Likewise, the observed β-adrenergic blocking activity of these pyridines indicates that they are useful in humans as β-adrenergic blocking agents.

For use as antihypertensives and/or β-adrenergic blocking agents, the compounds of the present invention can be administered orally, by inhalation, by suppository or parenterally i.e. intravenously, intraperitoneally, etc. and in any suitable dosage form. The compounds may be offered in a form (1) for oral administration e.g. as tablets in combination with other compounding ingredients (diluents or carriers) customarily used such as talc, vegetable oils, polyols, benzyl alcohols, starches gelatin and the like—or dissolved, dispersed or emulsified in a suitable liquid carrier—or in capsules or encapsulated in a suitable encapsulating material; or (2) for parenteral administration, dissolved, dispersed, or emulsified in a suitable liquid carrier or diluent or (3) as an aerosol or (4) as a suppository. The ratio of active ingredient (Formula I pyridine) to compounding ingredients will vary as the dosage form requires. Concentional procedures are used to prepare the pharmaceutical formulations.

The dosage level for the present compounds may be varied from about 0.01 mg. to about 50 mg. per kilogram of animal body weight per day. Daily doses ranging from about 0.04 to about 2.5 mg/kg are preferred, with about 0.08 to about 1.35 mg/kg being a more preferred range. Oral administration is preferred. Either single or multiple daily doses may be administered depending on unit dosage.

Thus, another embodiment of this invention is a pharmaceutical composition containing an antihypertensive and/or β-adrenergic blocking amount of a Formula I compound of the present invention.

Other embodiments of the present invention are the halopyridine intermediates of Formula III namely

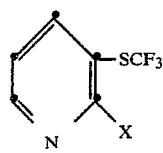

III and the method of their preparation according to the process illustrated by the following set of reactions.

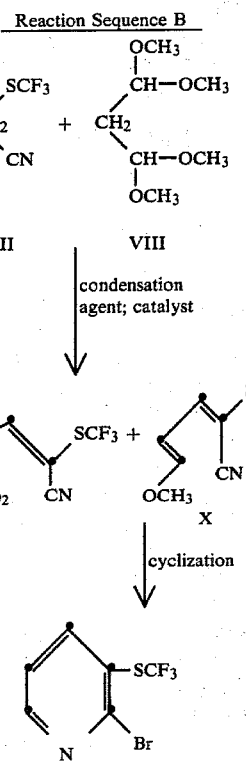

Condensation agent may be an organic acid anhydride e.g. acetic anhydride and the catalyst is preferably a metallic halide such as $ZnCl_2$. The cyclization is effected in a suitable system such as H Br and acetic acid.

The following examples illustrate the preparation of (1) a formula III intermediate using the Sequence B process and (3) a representative compound of Formula I. All temperatures are in degrees Celsius.

EXAMPLE I

Preparation of 2-bromo-3-trifluoromethylthiopyridine

A solution of acetic anhydride (52 mL), 1,1,3,3-tetramethoxypropane (26.4 g, 0.16 mL), trifluoromethylthioacetonitrile (14.5 g, 0.1 mol) and $ZnCl_2$ (1 g) was heated at reflux. After 18 hours, the mixture was distilled up to 100° at atmospheric pressure. The residue was then cooled to 25° C. and filtered. The clear solution was distilled to yield 3.5 g of 4-cyano-4-trifluoromethylthio-3-butenealdehydedimethylacetal (bp 65°–93° C. at 18 mm) and 5.3 g of 1-cyano-1-trifluoromethylthio-4-methoxy-1,3-butadiene (bp 83°–105° C. at 0.5 mm). This material was combined and used in the next step without further purification.

A solution of 30% HBr, AcOH (70 mL) was added dropwise with stirring at 40° C. to a solution of 4-cyano-4-trifluoromethylthio-3-butenealdehydedimethylacetal and 1-cyano-1-trifluoromethylthio-4-methoxy-1,3-butadiene (8.8 g) in AcOH (40 mL). After the addition, the solution was heated at 55° C. for 2 hours, poured onto ice and neutralized with solid $Na_2CO_3$. The solution was extracted with $CH_2Cl_2$ (3x) and the $CH_2Cl_2$ extracts dried, filtered and concentrated to dryness. The residual oil was distilled at 68°–71° C. at 0.3 mm of yield 4.0 g (16%) of 2-bromo-3-trifluoromethylthiopyridine $^1H$ NMR $(CDCL_3)$ δ7.35 (1H, dd, J=4 and 8), 8.05 (1H, dd, J=2 and 8), 8.45 (1H, dd, J=3 and 4); $^{19}$F NFR (CDCl$_3$)+40.7 (s).

The exact mass was 256.9130 (calcd for C$_6$H$_3$NBr$^{79}$SF$_3$, 256.9122) and 258.9130 (calcd for C$_6$H$_3$NBr$^{81}$SF$_3$, 258.8102).

EXAMPLE 2

(S) 2-(3-tert-butylamino-2-hydroxypropoxy)-3-trifluoromethylthiopyridine maleate salt Into a flame dried flask under N$_2$ is placed tert-butanol (200 ml), potassium metal (0.7 g, 0.018 mol) and (S) 2-phenyl-3-tert-butyl-5-hydroxymethyloxazolidine (5.0 g, 0.02 mol) and the mixture heated at 40° C. with stirring. After the potassium metal had reacted, a solution of 2-bromo-3-trifluoromethylthiopyridine (4.0 g, 0.015 mol) in tert-butanol (100 ml) was added dropwise. After the addition, the solution was heated at 70°–80° C. for 15 hours. The tert-butanol was removed under reduced pressure, H$_2$O added to the residue and the pH of the resulting solution adjusted to pH 2–3 with 3 N HCl. After stirring for 45 minutes at 25° C., the aqueous layer was extracted with Et$_2$O (2x), poured into saturated Na$_2$CO$_3$ solution and extracted with CHCl$_3$ (3x). The CHCl$_3$ layer was dried over Na$_2$SO$_4$, filtered and concentrated to dryness. The residue was chromotographed on silica gel and the product eluted with 20% CH$_3$OH-CHCl$_3$ to yield 1.4 g (29%) of the free base 2-(3-tert-butylamino-2-hydroxypropoxy)-3-trifluoromethylthiopyridine). The residue was crystallized as the maleate salt from EtOH-Et$_2$O to yield 0.8 g of (S) 2-(3-tert-butylamino-2-hydroxypropoxy)-3-trifluoromethylthiopyridine maleate salt m.p. 108°–100° C.

What is claimed is:

1. A compound having the formula

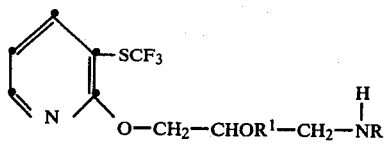

and pharmaceutically acceptable salts thereof wherein R is H or C$_1$–C$_6$alkyl and R$^1$ is H or

wherein L is C$_1$–C$_{10}$alkyl, phenyl or substituted phenyl having up to two substituents independently selected from C$_1$–C$_4$alkoxy, halo and C$_1$–C$_4$alkyl.

2. A compound of claim 1 wherein R is C$_3$–C$_4$ branched alkyl.
3. A compound of claim 1 wherein R$^1$ is H.
4. A compound of claim 3 wherein R is isopropyl or t-butyl.
5. A compound of claim 4 wherein R is isopropyl.
6. A compound of claim 4 wherein R is t-butyl.
7. The S-isomer of the compound of claim 1.
8. A pharmaceutical composition for treating hypertension containing an effective amount of the compound of claim 1 and a carrier.

* * * * *